United States Patent [19]

Blacker et al.

[11] Patent Number: 5,527,916

[45] Date of Patent: Jun. 18, 1996

[54] PYRANONES

[75] Inventors: Andrew J. Blacker, North Rigton; John Crosby, Bowden; John A. L. Herbert, Ramsbottom, all of England

[73] Assignee: Zeneca Limited, London, England

[21] Appl. No.: 211,043

[22] PCT Filed: Sep. 11, 1992

[86] PCT No.: PCT/GB92/01666

§ 371 Date: Aug. 1, 1994

§ 102(e) Date: Aug. 1, 1994

[87] PCT Pub. No.: WO93/06236

PCT Pub. Date: Apr. 1, 1993

Related U.S. Application Data

[62] Division of Ser. No. 946,194, Sep. 17, 1992, Pat. No. 5,443,971.

[30] Foreign Application Priority Data

| Sep. 20, 1991 | [GB] | United Kingdom | 9120110 |
| Sep. 20, 1991 | [GB] | United Kingdom | 9120134 |
| Sep. 20, 1991 | [GB] | United Kingdom | 9120138 |
| Sep. 20, 1991 | [GB] | United Kingdom | 9120152 |
| Sep. 20, 1991 | [GB] | United Kingdom | 9120153 |
| Sep. 20, 1991 | [GB] | United Kingdom | 9120157 |
| Sep. 20, 1991 | [GB] | United Kingdom | 9120173 |
| Jun. 4, 1992  | [GB] | United Kingdom | 9211795 |

[51] Int. Cl.$^6$ .................... C07D 277/04; C07D 309/30
[52] U.S. Cl. ................... 548/200; 548/236; 548/311.1; 549/214; 549/218; 549/291
[58] Field of Search ..................... 549/291, 214, 549/218; 548/200, 236, 311.1

[56] References Cited

U.S. PATENT DOCUMENTS 4,625,039  11/1986  Jewell, Jr. et al. .................... 549/214

FOREIGN PATENT DOCUMENTS

| 0271432 | 6/1988 | European Pat. Off. . |
| 0428392 | 5/1991 | European Pat. Off. . |
| 0439779 | 8/1991 | European Pat. Off. . |
| WO86/00307 | 1/1986 | WIPO . |

OTHER PUBLICATIONS

Cardani et al, S. Tetrahedron 46(20) pp. 7283–7288 (1990).

*Primary Examiner*—C. Warren Ivy
*Assistant Examiner*—Amelia Owens
*Attorney, Agent, or Firm*—Cushman Darby & Cushman

[57] ABSTRACT

A process for the separation of at least one isomer from a mixture of isomers of a tetrahydropyran-2-one, having at least two chiral centers which comprises selective reaction of at least one isomer with a reagent catalyzed by a hydrolase enzyme whereby at least one isomer is preferentially converted into a distinct chemical species from the other isomers so that it is susceptible of separation by an appropriate chemical or physical separation process in which the tetrahydropyran-2-one is of Formula (1):

Formula (1)

wherein:
  Z is —H or a protecting group susceptible of reaction with the reagent under the influence of the enzyme; and
  Y is formyl or protected formyl.

7 Claims, No Drawings

PYRANONES

This is a 371 of PCT/GB92/01666 filed Sep. 11, 1992 and a divisional application of U.S. Ser. No. 07/946,194, filed Sep. 17, 1992, now U.S. Pat. No. 5,443,971.

This invention relates to processes for the preparation of tetrahydropyran-2-ones which involve a kinetic resolution stage for producing at least one optically active isomer of a tetrahydro pyran-2-one having at least two chiral centres from a mixture of isomers, such as a cis or trans racemate or a mixture of cis and trans racemates, to certain novel isomers, particularly single enantiomers, of the tetrahydropyran-2-one, and to certain novel dihydropyran-2-ones and pyran-2-ones.

Optically active materials such as tetrahydropyran-2-ones may be used as intermediates in the manufacture of compounds such as pharmaceuticals, agrochemicals and chemicals for use in electronics industry. The optically active tetrahydropyran-2-ones of the present invention are particularly useful as intermediates in the manufacture of HMG-CoA reductase inhibitors. Available processes for the production of tetrahydropyran-2-ones are typically lengthy, require reagents which are expensive or difficult to handle on a large scale, give poor overall yields, and do not give access to all optical isomers.

According to the present invention there is provided a process for the separation of at least one isomer from a mixture of isomers of a tetrahydropyran-2-one, having at least two chiral centres, which comprises selective reaction of at least one isomer with a reagent catalysed by a hydrolase enzyme whereby at least one isomer is preferentially converted into a distinct chemical species from the other isomers so that it is susceptible of separation by an appropriate chemical or physical separation process in which the tetrahydropyran-2-one is of Formula (1):

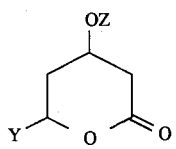

Formula (1)

wherein:

Z is —H or a protecting group susceptible of reaction with the reagent under the influence of the enzyme; and Y is formyl or protected formyl.

The protecting group, Z, is preferably a readily displaceable protecting group. Examples of suitable readily displaceable protecting groups include —PO.(OR$^3$)$_2$, —CO.R$^3$; —SO.OR$^3$; —NO$_2$ and —(CO).OR$^3$ in which each R$^3$ is independently optionally substituted alkyl, optionally substituted alkenyl or optionally substituted phenyl. Preferred examples of the protecting group, Z, include benzoyl, —COCH$_3$, —CO(n—C$_3$H$_7$) and —(CO)OCH$_3$.

Where the group represented by Y is protected formyl it is preferably of the formula —CH(OR)$_2$, —CH(SR)$_2$ or —CH(OR)(SR) wherein each R independently is —H, optionally substituted alkyl, optionally substituted alkenyl or optionally substituted phenyl or two groups —OR or —SR attached to the same carbon atom, together with the carbon atom to which they are attached, form a 5- to 7-membered heterocycle. Examples of such groups are:

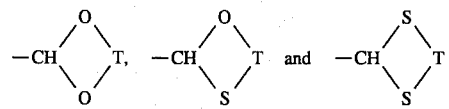

in which each T is a divalent group. Examples of suitable groups represented by T are —C$_2$H$_4$—, —(CH$_2$)$_3$—, —CH(CH$_3$)—CH(CH$_3$)— and —CH(Ph)—CH(Ph)—. Alternatively, the formyl group may be protected by conversion into an oxazolidine, imidazolidine, thiazolidine, bisulphite, O-substituted cyanohydrin such as O-acyl, O-tetrahydropyran-2-yl and O—SiR$^3$ in which R$^3$ is as hereinbefore defined, cyanohydrin, hydrazone or oxime derivative. It is preferred that the formyl group is protected by conversion into an oxazolidine.

Where R or R$^3$ is or contains an alkyl group this is preferably C$_{1-12}$-alkyl, more preferably C$_{1-6}$-alkyl and especially methyl, ethyl, propyl or butyl.

Where R or R$^3$ is or contains an alkenyl group this is preferably C$_{2-12}$-alkenyl, more preferably C$_{2-6}$-alkenyl and especially vinyl. Where any R or R$^3$ is alkyl or alkenyl it may be in the form of a straight or R$^3$branched chain.

Where the group represented by R or is optionally R$^3$ is optionally substituted alkyl or alkenyl, the substituent is preferably selected from C$_{1-6}$-alkoxy; halogen, such as —Cl, —Br or —F; hydroxy; cyano; —NR$_2$ in which R is as hereinbefore defined such as —NMe$_2$; cyclohexyl; phenyl; and protected primary and secondary amino groups such as —NHCOMe and —N(SiMe$_3$)$_2$. Where the group represented by R or R$^3$ is optionally substituted phenyl, the substituent is preferably selected from C$_{1-6}$-alkyl, especially methyl; C$_{1-6}$-alkoxy, especially methoxy; cyclohexyl; phenyl; nitro; hydroxy; cyano; halogen, especially Cl, Br, or F; —NR$_2$ in which R is as hereinbefore defined such as —NMe$_2$; and protected primary and secondary amino groups such as —NHCOMe and —N(SiMe$_3$)$_2$.

Examples of particularly preferred groups represented by Y are CO.H, —CH(OCH$_3$)$_2$, —CH(OPh)$_2$, —CH(OC$_2$H$_5$)$_2$, —CH(SC$_2$H$_5$)$_2$, —CH(OC$_2$H$_5$)(SC$_2$H$_5$),

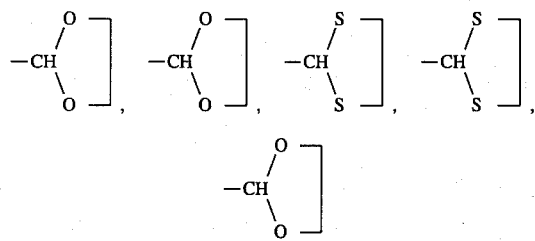

or a formyl group protected by formation of an oxazolidine with ethanolamine or by formation of an imidazolidine by reaction with 1,2-ethylenediamine, or by formation of a thiazolidine by reaction with a 2-aminoethanethiol.

The enzyme catalysed reaction is a kinetic resolution which means that the reaction occurs because the enzyme catalyses the reaction of the reagent with different isomers at different rates. A compound with two chiral centres may consist of a mixture of four isomers i.e. two pairs of enantiomers, and a suitable enzyme catalyses reaction of the reagent with each isomer at a different rate so that over a period of time the composition changes from a mixture of, for example 4 isomers to a mixture of 3 isomers and a more distinct chemical species which can be separated from the unchanged isomers by appropriate conventional separation techniques; or one enantiomer of an enantiomer pair is similarly changed to a distinct chemical species which may be similarly separated.

The nature of the reagent and the enzyme depends upon the nature of the group —OZ and the stereochemistry of the isomer(s) with which the reagent is to react. Where Z is —H the selective reaction is conveniently a trans-esterification or esterification and the reagent is an ester or acid capable of reaction with the group —OH when catalysed by the enzyme. In this process the group —OH in the selected isomer(s) is converted into an ester so that the isomer(s) is/are chemically distinct and can be readily separated from the other isomer(s) in which Z is still —H. In this reaction, the enzyme preferably causes the group $R^4CO$— of an ester, $R^4COOR^5$ or an acid $R^4COOH$ (in which $R^4$ and $R^5$ each independently is optionally substituted alkyl, alkenyl or aryl) to react preferentially with a group —OZ in one, or all except one, isomer in the mixture. It is preferred that the $R^4CO$— portion is preferentially attacked by the group —OH in one, or all except one, of the isomers in the mixture.

The alkyl and alkenyl groups represented by $R^4$ and $R^5$ are preferably $C_{1-18}$-alkyl and $C_{2-18}$-alkenyl, more preferably $C_{1-6}$-alkyl and $C_{2-5}$-alkenyl, especially $C_{1-4}$-alkyl and vinyl and allyl respectively and may be straight or branched chain alkyl. The aryl groups represented by $R^4$ and $R^5$ are preferably phenyl or naphthyl each of which may be optionally substituted. Where the groups $R^4$ and $R^5$ are optionally substituted the substituent may be selected from any of those described above for R. $R^5$ is preferably an alkenyl group, more preferably a $C_{2-3}$-alkenyl group and especially vinyl. $R^4$ is preferably an alkyl group, more preferably a $C_{1-4}$-alkyl group and especially methyl, ethyl or n-propyl. The ester of the formula $R^4COOR^5$ may be an alkyl ester, e.g. an alkyl alkanoate, such as methyl acetate, methyl butyrate or ethyl acetate or an alkyl benzoate, such as methyl benzoate, but is preferably a non-reversible acyl donor, especially an alkenyl ester, more preferably an alkenyl alkanoate such as vinyl acetate or vinyl butyrate.

Scheme 1 illustrates a trans-esterification process where the reagent is $R^4COOR^5$ or an esterification process whre the reagent is $R^4COOH$ for a mixture of isomers of Formula (1) in which Z is —H and Y is as hereinbefore defined:

Scheme 1

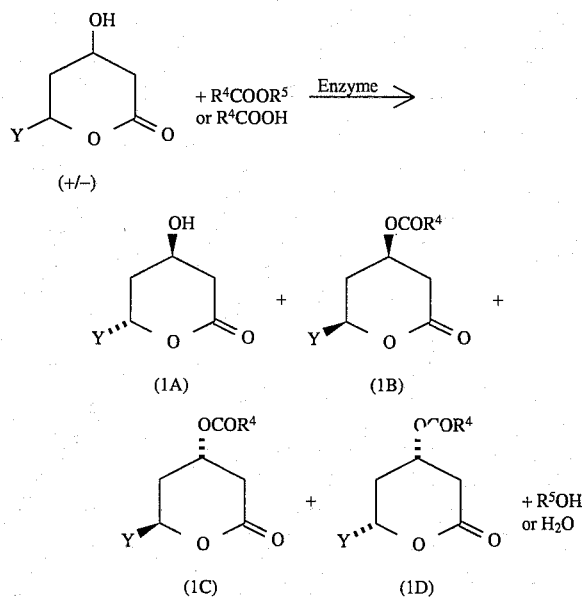

In Scheme 1, Compounds 1B, 1C & 1D are isomeric esters formed by preferential esterification of the corresponding alcohol isomers in the mixed isomer starting material and are distinct chemical species from the unchanged alcohol, Compound 1A. The latter may be separated from the former by any convenient means such as chromatography, solvent extraction, crystallisation or distillation.

The trans-esterification and esterification reactions may be performed in a two phase liquid medium comprising water and an immiscible organic liquid. Where two phases are present the enzyme partitions predominantly into the aqueous phase and thus the enzyme catalysed reaction occurs mainly in the aqueous phase. In the aqueous phase the equilibrium position of the trans-esterification and esterification reactions may be shifted resulting in a decreased yield of the required product. Thus, the trans-esterification or esterification reaction is preferably performed in a single phase organic liquid medium which contains small amounts of water.

By small amounts of water it is meant that water immiscible organic liquids contain less than or equal to the amount of water required to saturate the organic liquid and water miscible organic liquids contain less than 50%, preferably less than 20% and especially less than 10% water.

When water is present in predominantly organic systems the concentration of water may not be very meaningful and the system may be better defined using the thermodynamic activity of water (Aw). Aw values may be measured via relative humidity in an equilibrated gas phase as described in EP 64855A. Water under standard state conditions has by definition an Aw value of 1. For the trans-esterification reaction the activity of water (Aw) in the organic liquid is less than 1 and greater than 0.05, preferably from 0.95 to 0.1.

The reaction medium may comprise one or more of the participating species, such as the tetrahydropyran-2-one or the ester $R^4COOR^5$ or the acid $R^4COOH$ or a substantially inert organic liquid or a mixture of such liqiuds. Suitable inert organic liquids include a straight or branched chain alkane, especially a $C_{5-16}$-alkane such as hexadecane, isooctane or hexane; an optionally substituted arene, especially an optionally substituted benzene such as toluene or xylene; an optionally substituted ether, especially a $C_{1-5}$-alkoxy-$C_{1-5}$-alkane such as t-butoxymethane or ethoxyethane; a $C_{4-8}$-cyclic ether such as tetrahydrofuran or 1,4-dioxane; a halogenated alkane, especially a halogenated $C_{1-3}$-alkane such as dichloromethane, trichloromethane, tetrachloromethane or 1,1,2-trichloroethane; a carboxylic acid, especially a $C_{1-3}$-carboxylic acid such as ethanoic or propanoic acid; an alkyl cyanide, especially a $C_{1-3}$-alkylcyanide such as acetonitrile; an alkyl alkanoate, especially a $C_{1-5}$-alkyl $C_{1-5}$-alkanoate such as i-propyl acetate, methyl butyrate or ethyl acetate; an alkyl benzoate, especially a $C_{1-5}$-alkyl benzoate, such as methyl benzoate or ethyl benzoate; an alkenyl alkanoate, especially a $C_{2-5}$-alkenyl $C_{1-5}$-alkanoate such as vinyl acetate or vinyl butyrate; or an optionally branched alkanol, especially a $C_{1-10}$-alkanol, and more especially a $C_{1-6}$-alkanol, such as butan-1-ol, butan-2-ol, t-butanol, propan-2-ol, ethanol or methanol.

Where Z is a protecting group the selective reaction is conveniently a hydrolysis and the reagent is a hydrolytic agent, such as water or an alkanol, ROH in which R is as hereinbefore defined, which is capable of replacing the protecting group Z by H when catalysed by the enzyme. In this process the group OZ in the selected isomer(s) is converted into an OH group so that the selected isomer(s)

is/are chemically distinct and can be readily separated from the other isomer(s) in which Z is still a protecting group. In this reaction the enzyme preferably catalyses the hydrolysis of one or more isomers in a mixture of isomers of Formula (1) in which Z is a protecting group, such as —CO.R$^4$ Scheme 2 illustrates the hydrolysis of a mixture of isomeric esters of Formula (1) in which Z is —CO.R$^4$ and R$^4$ and Y are as hereinbefore defined:

Scheme 2

Scheme 2

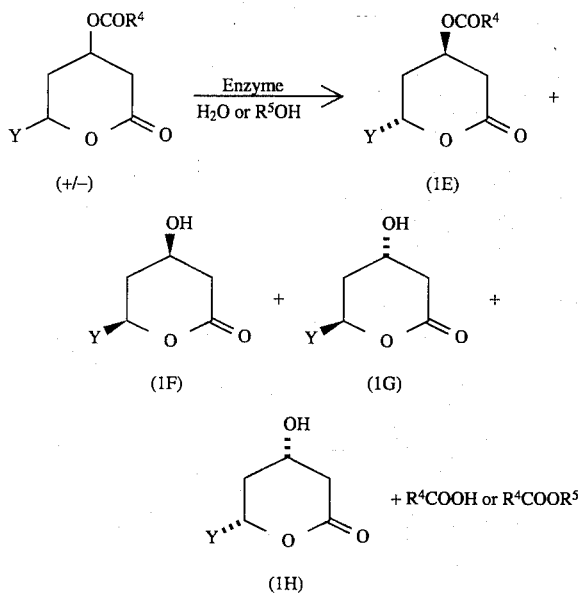

In Scheme 2, Compounds 1F, 1G and 1H are alcohols formed by preferential hydrolysis of the corresponding esters in the starting material and these are distinct chemical species from the unchanged ester, Compound 1E. The former may be separated from the latter by any convenient means such as chromatography, solvent extraction, crystallisation or distillation. Once separated Compound 1E may be chemically hydrolysed to the corresponding hydroxy compound.

The enzymatic hydrolysis reaction may be performed in a liquid medium such as water, an organic liquid or a mixture thereof. Suitable organic liquids for the hydrolysis are those described above for the trans-esterification. Where the liquid medium comprises water or an alkanol, the water or alkanol may form only a proportion of the liquid medium, e.g. from 1% to 50% thereof, depending on the equilibrium constant for the system, and may be buffered at a pH from 4 to 10, preferably from 4 to 9 and especially from 6 to 8. The buffer may be inorganic or organic and is preferably an inorganic phosphate such as sodium or potassium phosphate or an organic amine salt, such as the hydrochloride, acetate, phosphate or benzoate salt of tri(hydroxymethylamino)methane.

The reaction medium for the trans-esterification, esterification or the hydrolysis may further comprise components which stabilise the enzyme and maximise its catalytic efficiency. Such components may comprise cations, especially H$^+$ and H$_3$O$^+$; alkali metal cations such as Li$^+$, Na$^+$ and K$^+$; alkaline earth cations such as Mg$^{2+}$ and Ca$^{2+}$, Group III metal cations such as Al$^{3+}$; transition metal cations such as Zn$^{2+}$, Fe$^{2+}$, Cu$^{2+}$, Co$^{2+}$ and Ni$^{2+}$; and/or ammonium and substituted ammonium cations such as NR$_4^+$ in which each R independently is as hereinbefore defined. Other suitable components may comprise anions, especially halides such as F$^-$, Cl$^-$, Br$^-$ and I$^-$; oxyphosphorus anions such as HPO$_4^{2-}$ and PO$_4^{3-}$; oxysulphur anions such as SO$_4^{2-}$; oxynitrogen anions such as NO$_3^-$; OH$^-$; CO$_3^{2-}$ and/or organic anions such as formate, acetate, oxalate, tartrate, malonate or succinate. The preferred cations and anions may be used in combination or as salts with other anions and cations, respectively. Salts containing these ions may be employed undissolved in the reaction medium in order to change the state of hydration and thus the activity of water in the medium. For example when sodium carbonate decahydrate is added to the reaction medium it becomes sodium carbonate monohydrate by losing 9 equivalents of water, in this way a known amount of water may be added to the reaction medium.

To this end the salts may be hydrated salts or mixtures of anhydrous and hydrated salts (see Biochim, Biophys Acta (1991) 1078, 326). The hydrolysis medium may also contain antioxidants such as ascorbates or thiols, such as dithiothreitol, 2,3-dimethylpropanethiol, ethanethiol and cysteine.

The trans-esterification, esterification and hydrolysis reactions may be performed at temperatures from 0° C. to 100° C., preferably from 10° C. to 60° C. more preferably from 25° C. to 60° C. and especially from 30° C. to 60° C. During the course of the hydrolysis reaction an inorganic base, preferably an alkali metal hydroxide such as sodium hydroxide, may be added to maintain the pH of the reaction mixture. The reaction medium may be agitated by appropriate methods such as stirring, shaking or sonicating.

The hydrolase enzyme is preferably an esterase, lipase, nitrilase, amidase, peptidase, glycosidase or phosphatase derived from microbial, animal or plant sources. Especially preferred enzymes are Chromobacterium viscosum lipase from Biocatalysts Ltd, AMANO P lipase from Amano Pharmaceuticals (AMANO is a trade mark of Amano Pharmaceuticals), Pseudomonas fluorescens lipase from Biocatalysts or Fluka Chemie AG, Mucor miehi strain such as NOVO IM60 and NOVO lypozyme from Novo Industrie (NOVO is a trade mark of Novo Industrie) or Lipoprotein lipase from Pseudomonas species, from Boehringer Mannheim GmbH or Fluka Chemie AG.

Suitable forms are microbial whole cell preparations or fractions derived from microbial, plant and animal tissues containing the required hydrolase activities. Such fractions include secreted enzymes, broken cells, cell-free extracts and purified hydrolase enzymes. The hydrolase enzyme may be prepared and used in the reaction as a lyophilised solid or water-containing liquid. When the hydrolase enzyme is prepared as a lyophilised solid it may further comprise components to stabilise the enzyme system and maximise its catalytic activity and antioxidants as described above.

The lyophilised solid may further comprise organic additives such as sugars, preferably glucose, mannose or trehalose; or polyols such as polyethyleneglycol; or detergents such as alkylammonium salts or alkylsulphonate salts. The hydrolase enzyme may be coated, for example by passive adsorption onto an inorganic or organic support material or covalently bonded onto an inorganic or organic support material. The inorganic support material may be a powdered or beaded silicate; an infusorial material, such as diatomaceous earth; zeolite; montmorillonite clay; or finely divided carbon such as charcoal or a polyphosphazene. A preferred inorganic support material is a beaded glass, sand, silica gel;

a diatomaceous earth such as CELITE (CELITE is a trade mark of Johns Manville Corporation); a molecular sieve (e.g. 4A); or charcoal. A convenient organic support is a resin such as EUPERGIT C (EUPERGIT is a trade mark of Rohm Pharma); an ionic exchange resin; a polysaccharide; a polyacrylamide; a protein; a nucleic acid; a lipid; a detergent capable of forming micelles; or a liposome. A preferred organic support material is an anionic exchange resin or a cellulosic material such as SEPHAROSE (SEPHAROSE is a trade mark of Pharmacia, Sweden).

The hydrolase enzyme may be prepared for use in the hydrolysis reaction as a stock solution in an aqueous liquid medium containing components which stabilise, maximise its catalytic activity and prevent its oxidation as described above. The same stock solution may be freeze dried at a temperature from −70° C. under vacuum until almost dry to give a hydrolase enzyme residue which is suitable for use in the trans-esterification or esterification reactions. However, it is important that the reaction medium for the trans-esterification and esterification reactions contains at least some water otherwise the hydrolase enzyme is ineffective as a trans-esterification or esterification catalyst. Thus either the enzyme residue must contain some water of water must be added to the trans-esterification or esterification medium.

A compound of Formula (1) in which Y is protected formyl such as —CH(OR$^3$)$_2$ may be prepared a) by reaction of the corresponding compound in which Y is —CHO with an alcohol, R$^3$OH in which R$^3$ is as hereinbefore defined, in the presence of dry hydrogen chloride or b) by reaction of a compound of Formula (1) in which Y is —CHX$_2$ with R$^3$OH in the presence of a silver salt such as silver nitrate. A compound of Formula (1) in which Y is protected formyl such as —CH(SR$^3$)$_2$ may be prepared by reaction of the corresponding compound in which Y is —CHO with a thiol, R$^3$SH in which R$^3$ is as hereinbefore defined, in the presence of BF$_3$.Et$_2$O. A compound of Formula (1) in which Y is protected formyl such as —CH(OR$^3$)(SR$^3$) may be prepared by reaction of the corresponding compound in which Y is —CHO with a mixture of alcohol, R$^3$OH and thiol R$^3$SH in which R$^3$ is as hereinbefore defined.

Compounds of Formula (1) in which Y is protected formyl such as —CH(OR$^3$)$_2$, —CH(SR$^3$)$_2$ or —CH(OR$^3$)(SR$^3$) in which the R$^3$ groups are joined to form a 5- to 7-membered heterocycle may be formed by reaction of the corresponding compound of Formula (1) in which Y is —CHO with a diol such as ethan-1,2-diol, a dithiol such as propan-1,3-dithiol or a hydroxythiol such as 2-hydroxyethanethiol. A compound of Formula (1) in which Y is oxazolidinyl, imidazolidinyl or thiazolidinyl, i.e. a protected formyl group, may be prepared by reaction of the corresponding compound of Formula (1) in which Y is —CO.H or —CHX$_2$ (in which X is halogen) with a 1-hydroxy-2-amino alkane such as an ethanolamine, or a 1,2-diamino alkane such as an ethylenediamine, or a 1-thiol-2-aminoalkane such as an aminoethanethiol, respectively. Where the formyl group is protected by conversion into a bisulphite, cyanohydrin, an O-substituted cyanohydrin, hydrazone or oxime derivative these may be formed by reaction of the formyl compound with sodium bisulphite, hydrogen cyanide, acetonecyanohydrin, Me$_3$SiCN/KCN, hydrazines or hydroxylamines respectively.

The formyl group of compounds of Formulae (2) and (3) in which Y is formyl and of Formula (10) may also be protected as described above. The reactions to protect the formyl group form a further feature of the present invention.

The 4-hydroxy group, in the the compound of Formula (1) in which Z is H, may be protected for example by reaction with a compound of formula Z—X (wherein Z is as hereinbefore defined except —H and —NO$_2$ and X is halogen, especially —Cl or —Br). Compounds of Formula (1) in which Z is —NO$_2$ may be prepared by reaction of the corresponding compound of Formula (1) in which Z is mesyl with a tetraalkylammonium nitrate. Further details of reactions for the preparation of —OZ compounds in which Z is a protecting group are described in 'Protective Groups in Organic Synthesis', T. W. Greene and P. G. M. Wuts published by Wiley & Sons 2nd Edition (1991).

According to a further feature of the present invention there is provided a process for the preparation of a tetrahydropyran-2-one of the Formula (1):

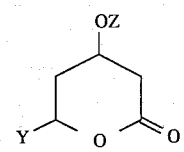

Formula (1)

by reduction of a dihydropyran-2-one of Formula (2):

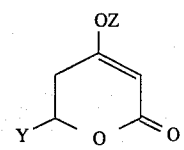

Formula (2)

wherein:

Y and Z are as hereinbefore defined.

This process may be performed by chemical reduction, where the compound of Formula (2) preferably in a liquid medium, is reacted with hydrogen in the presence of a catalyst. The liquid medium is preferably an organic liquid, and more preferably an alcohol, especially a lower alkanol such as ethanol, n-propanol or isopropanol or water or a mixture of water and lower alkanol such as water/ethanol or an ester such as ethylacetate or isopropylacetate. Suitable catalysts are metal catalysts preferably those where the metal is from Group VIII of the Periodic Table. The catalyst is preferably a finely divided metal or is a metal carried on a support such as carbon or aluminium oxide. An especially preferred catalyst is Raney nickel. The process is preferably performed at a temperature from 0° C. to 120° C., more preferably from 10° C. to 80° C. and especially from 20° C. to 50° C. The process is conveniently carried out at the boiling point of the liquid medium and at a pressure from 1×10$^4$ Pa to 1×10$^6$ Pa, preferably from 5×10$^4$ Pa to 5×10$^5$ Pa and especially at from 8×10$^4$ Pa to 2×10$^5$ Pa. The process is preferably continued until substantially all the starting material is consumed which may be detected by chromatographic analysis. The product may be isolated by removing the catalyst by filtration and evaporation of the liquid medium. The product may be purified by any convenient means such as distillation or crystallisation.

Where dihydropyran-2-ones of Formula (2) are already optically resolved at the 6-position chemical reduction of the double bond between the 3- and 4-positions with cis- or trans-control fixes the stereochemistry at the 4-position and individual enantiomers can be obtained. For example with cis-control enantiomers of Formulae (1J) or (1K) are obtained and with trans-control, enantiomers of Formulae (1I) or (1L) can be obtained. However, where dihydropyran-2-ones of Formula (2) are racemic, chemical reduction with no cis-trans selectivity, produces a mixture of isomers of Formulae (1I), (1J), (1K) and (1L):

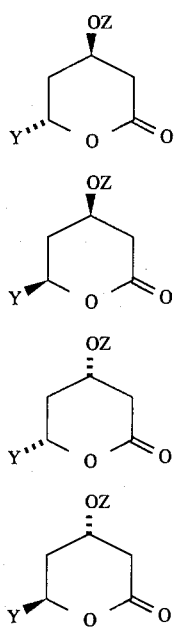

Formula (1I)

Formula (1J)

Formula (1K)

Formula (1L)

Separation of a mixture of isomers of Formulae (1I), (1J), (1K) and (1L) may be achieved by reacting the mixture with optically active α-methylbenzylamine to form the corresponding diastereomeric α-methylbenzylamide derivatives. The α-methylbenzylamide derivatives may be separated by any convenient means such as chromatography or crystallisation. After separation each α-methylbenzylamide derivative is firstly hydrolysed and then dehydrated to reform the individual isomers of Formulae (1I) to (1L).

According to a further feature of the present invention there is provided a process for the preparation of a dihydropyran-2-one of the Formula (2):

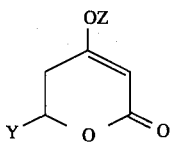

Formula (2)

by reduction of a pyran-2-one of the Formula (3):

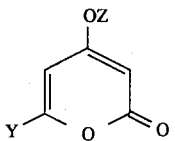

Formula (3)

wherein:

Y and Z are as hereinbefore defined.

The process may be performed by chemical reduction, where the compound of Formula (3) preferably in a liquid medium, is reacted with hydrogen in the presence of a catalyst. The liquid medium is preferably an organic liquid and especially an alkanol such as ethanol, or propanol or an ester such as ethylacetate. Suitable catalysts are metal catalysts preferably where the metal is from Group VIII of the Periodic Table. The catalyst is preferably a finely divided metal or metal supported on a carbon or aluminium oxide support and is optionally modified by pre-treatment before use in the process. The catalyst is preferably palladium on carbon with a metal loading of from 0.5 to 10% by weight preferably from 1 to 5% by weight. The process is preferably performed at a temperature from 0° C. to 80° C., preferably from 15° C. to 50° C., especially from 20° C. to 30° C. The process is preferably performed at a pressure from $1 \times 10^4$ Pa to $1 \times 10^7$ Pa, more preferably from $1 \times 10^5$ Pa to $1 \times 10^7$ Pa. The process is preferably continued until all the starting material is consumed. The product may be isolated by removing the catalyst by filtration and evaporation of the liquid medium. The product may be purified by any convenient means such as distillation or crystallisation.

According to the present invention there is provided a process for the resolution of dihydropyran-2-ones of the Formula (2):

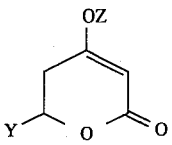

Formula (2)

which comprises a selective reaction of one enantiomer with a reagent catalysed by a hydrolase enzyme whereby the enantiomer is preferentially converted into a distinct chemical species from the other enantiomer so that it is susceptible of separation by an appropriate chemical or physical separation process, wherein Y and Z are as hereinbefore defined.

The conditions for trans-esterification, esterification and hydrolysis reactions described above for the resolution of compounds of Formula (1) are applicable to the resolution of compounds of Formula (2); although the especially preferred enzymes for the resolution of the compounds of Formula (2) are Pseudomonas fluorescens lipases from Biocatalysts or Fluka Chemie, Chromobacterium viscosum lipase from Biocatalysts, Candida cylindracae from Biocatalysts, Fluka Chemie or Sigma, Mucor Miehi from Biocatalysts or Fluka Chemie and Lipoprotein lipase from Boehringer Mannhelm or Fluka Chemie. The process may be illustrated by the following schemes whereby a racemate of Formula (2) may be resolved.

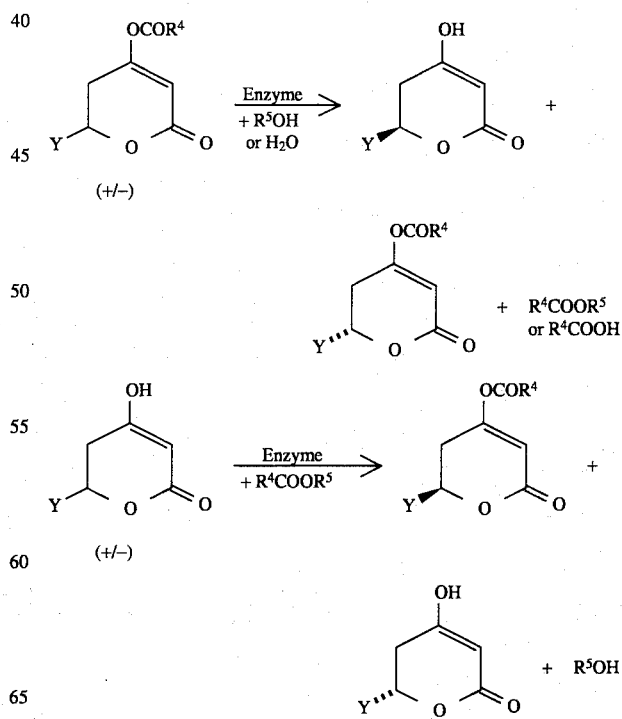

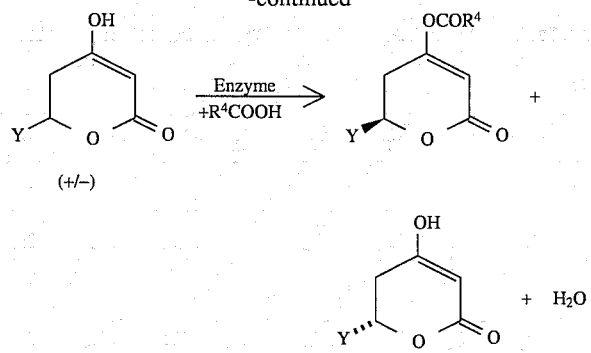

The products of these reactions may be separated by standard methods such as solvent extraction, chromatography or crystallisation.

According to a further feature of the present invention there is provided a process for the preparation of a tetrahydropyran-2-one of the Formula (1):

by reduction of a pyran-2-one of the Formula (3):

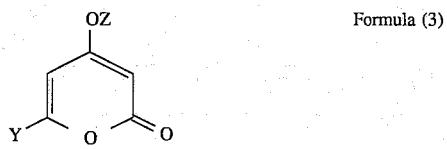

wherein:

Y and Z are as hereinbefore defined.

The process may be performed by chemical reduction where the compound of Formula (3) is reacted in a liquid medium with hydrogen in the presence of a catalyst. The liquid medium is preferably an organic liquid and more preferably an alkanol such as methanol, ethanol, n-propanol or n-butanol or an ester such as ethyl acetate. Alternatively, the liquid medium may be water or a mixture of water and alkanol such as water/ethanol. Suitable catalysts are metal catalysts preferably those where the metal is from Group VIII of the Periodic Table. The catalyst is preferably a finely divided metal or a metal carried on a support such as carbon, more preferably Raney Nickel. The process is preferably performed at a temperature from 20° C. to 130° C. and more preferably from 50° C. to 100° C. The process may be conveniently carried out at the boiling point of the liquid medium.

The process is performed at a pressure from $1 \times 10^4$ Pa to $1 \times 10^6$ Pa, preferably from $5 \times 10^4$ Pa to $5 \times 10^5$ Pa and especially from $8 \times 10^4$ Pa to $2 \times 10^5$ Pa. The process is preferably continued until substantially all the starting material is consumed. The product is isolated by removing the catalyst by filtration and evaporation of the liquid medium. The product is purified by any convenient means such as chromatography, distillation or crystallisation.

The hydrogenation of the pyran-2-one of Formula (3) to the tetrahydropyran-2-one of Formula (1) may be carried out in two stages without isolation of the intermediate dihydropyran-2-one of Formula (2), the first stage in the presence of a more selective catalyst, such as palladium on carbon and the second stage in the presence of a less selective catalyst, such as Raney nickel.

According to a further feature of the present invention there is provided a process for the preparation of a pyran-2-one of the Formula (3) in which Y is formyl by reaction of a pyran-2-one of the Formula (4):

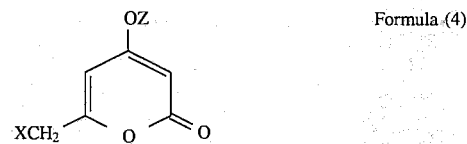

firstly with pyridine and secondly with a mixture of a nitroso compound and a base, wherein:

Z is as hereinbefore defined; and

X is halogen.

The halogen represented by X is preferably —Cl, —Br, —I, more preferably —Br.

This process may be performed by reaction of a compound of Formula (4) firstly with pyridine and secondly with a mixture of a nitroso compound and a base in a liquid medium. The liquid medium is preferably an aqueous alkanol, more preferably aqueous ethanol. The nitroso compound is preferably an aromatic nitroso compound such as 4-nitroso-N,N-dimethylaniline. The base is preferably an inorganic base such as potassium carbonate. The process is preferably carried out at a temperature from −10° C. to 50° C. more preferably from 0° C. to 30° C. The process is continued until substantially all the starting material is consumed. The intermediate "pyranyl N-oxide" is isolated by filtration of the reaction mixture and the pyran-2-one of Formula (3) in which Y is formyl is liberated by acidifying with an aqueous acid such as hydrochloric acid and extracting with an organic solvent followed by evaporation. The product is purified by chromatography as hereinbefore described.

According to a further feature of the present invention there is provided a process for the preparation of a pyran-2-one of the Formula (3) in which Y is formyl by oxidation of a pyran-2-one of the Formula (7):

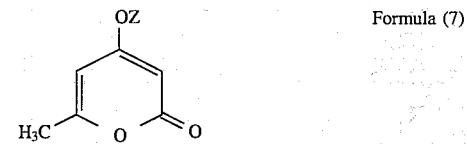

wherein:

Z is as hereinbefore defined.

This process may be performed by oxidation of a compound of Formula (7) in a liquid medium with an oxidising agent. The liquid medium is preferably an organic liquid, more preferably an ether such as dioxan. The oxidising agent is preferably selenium dioxide.

The process is preferably carried out at a temperature from 125° C. to 250° C. and more preferably from 160° C. to 200° C. The process is preferably carried out under pressure in a sealed vessel.

The process is continued until substantially all the starting material is consumed. The product is isolated by filtering the reaction mixture to remove the residual solids followed by evaporation of the liquid medium. The product may be purified by any convenient means such as chromatographing from a silica column using a mixture of methylene chloride/methanol as eluent.

According to a further feature of the present invention there is provided a process for the preparation of a pyran-2-one of the Formula (4):

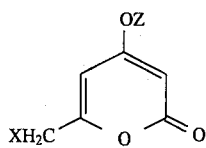

Formula (4)

by removal of a group W from a pyran-2-one of the Formula (5):

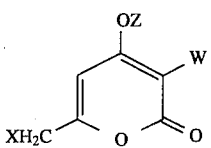

Formula (5)

wherein:

W is —COT$^1$ in which T$^1$ is an optionally substituted hydrocarbon group, —CHX$_2$, —CH$_2$X in which X is halogen; and Z is as hereinbefore defined.

In pyran-2-ones of Formula (5) W is preferably —COC$_{1-2}$-alkyl which may be optionally substituted by halogen.

The present process may be performed by heating the pyran-2-one of Formula (5) in a liquid medium in the presence of an acid. The acid is preferably an inorganic acid, more preferably H$_2$SO$_4$. The process is preferably performed at a temperature from 50° C. to 200° C., more preferably at from 80° C. to 150° C. and especially at from 80° C. to 135° C. The process is preferably continued until all the starting material is consumed. The product may be isolated by neutralising the reaction mixture and extracting with a solvent and evaporating the solvent. The product may be purified by any convenient method such as distillation or crystallisation.

The removal of a group W is not limited to the present pyran-2-one of Formula (5) and may be conveniently carried out at any stage in the overall process, i.e. if a pyran-2-one of Formula (3) or (6) below carries a group W in the 3-position this may be removed under similar conditions to those described above.

According to a further feature of the present invention there is provided a process for the preparation of a pyran-2-one of the Formula (5):

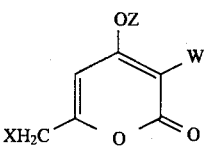

Formula (5)

by halogenation of a pyran-2-one of the Formula (6):

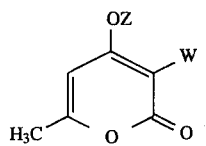

Formula (6)

wherein:

W, X and Z are as hereinbefore defined.

The present process may be performed by halogenation of a pyran-2-one of Formula (6) in a liquid medium with a halogenating agent, optionally in the presence of ultraviolet light and optionally in the presence of an organic peroxide to initiate the reaction.

The liquid medium is preferably an organic liquid which either does not itself undergo halogenation under the reaction conditions or which is already full halogenated. The organic liquid is preferably a haloalkane such as tetrachloromethane or hexachloroethane. The halogenating agent is preferably an N-halosuccinimide such as N-chlorosuccinimide for chlorination, N-bromosuccinimide for bromination.

Where an organic peroxide is used to initiate the reaction it is preferably an aromatic peroxide such as benzoyl peroxide or an aliphatic peroxide such as t-butyl hydroperoxide.

The process is preferably carried out at a temperature from 0° C. to 100° C., preferably from 30° C. to 80° C. and more preferably from 50° C. to 80° C. The reaction is continued until substantially all the starting material has been consumed. The product is isolated by evaporation of the liquid medium and purified by any convenient means such as column chromatography.

According to a further feature of the present invention there is provided a process for the preparation of a pyran-2-one of the Formula (8):

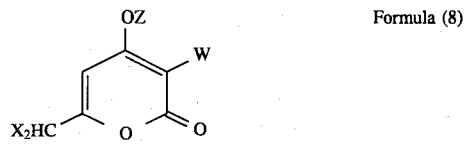

Formula (8)

by halogenation of a compound of the Formula (5):

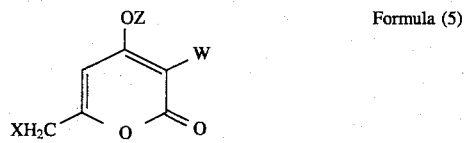

Formula (5)

wherein;

W, X and Z are as hereinbefore defined.

This process may be performed under the conditions described above for halogenation of a compound of Formula (6).

According to a further feature of the present invention there is provided a process for the preparation of a pyran-2-one of Formula (3) in which Y is —CH(OR)$_2$ by reaction of a pyran-2-one of Formula (8) in which Z is as hereinbefore defined, W is —H and X is halogen with a compound ROH wherein R is as hereinbefore defined in the presence of a silver salt. X is preferably —Cl or —Br, ROH is preferably an alkanol such as methanol or ethanol and silver salt is preferably silver nitrate. The process is preferably carried out at a temperature from 20° C. to 100° C. and is continued until substantially all the starting material is consumed. The product may be isolated by removal of the compound ROH and may be purified by any convenient means such as chromatograhpy.

According to a further feature of the present invention there is provided a process for the preparation of a pyran-2-one of the Formula (10):

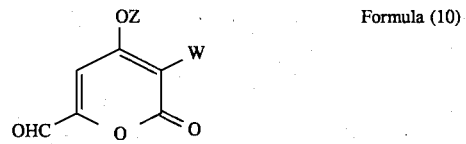

Formula (10)

by hydrolysis of a compound of the Formula (8):

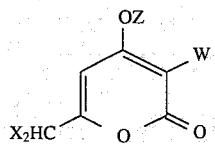

Formula (8)

wherein;

W, X and Z are as hereinbefore defined.

This process may be performed by hydrolysis of the compound of Formula (2) in a liquid medium. The liquid medium is preferably an alkanol such as methanol, ethanol or isopropanol or water or a mixture of alkanol and water. The hydrolysis may be effected in a number of ways by adding:

i) an acid, preferably an inorganic acid such as sulphuric acid or hydrochloric acid;
ii) a base preferably an inorganic base such as sodium or potassium hydroxide;
iii) by adding as silver nitrate; or
iv) a buffer to maintain the pH at approximately 7 to the compound of Formula (2) in the liquid medium. The process is preferably carried out at a temperature from 0° C. to 150° C. and more preferably from 50° C. to 120° C. and conveniently at the boiling point of the liquid medium. The process is continued until substantially all the starting material is consumed. The product is isolated by neutralisation of the reaction mixture, extraction with an organic liquid, separation and evaporation. The product is purified by any convenient means such as distillation or column chromatography.

According to a further feature of the present invention there is provided a process for the preparation of a pyran-2-one of the Formula (11):

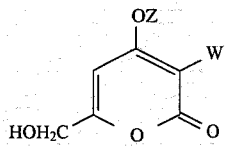

Formula (11)

by hydrolysis of a pyran-2-one of the Formula (5):

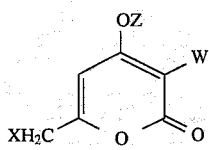

Formula (5)

wherein;

W, X and Z are as hereinbefore defined.

This process may be performed by hydrolysis of the compound of Formula (5) in a liquid medium.

The liquid medium is preferably an alkanol such as methanol, ethanol or isopropanol or water or a mixture of alkanol and water. The hydrolysis may be effected in a number of ways by adding:

i) an acid, preferably an inorganic acid such as sulphuric acid or hydrochloric acid;
ii) a base preferably an inorganic base such as sodium or potassium hydroxide;
iii) by adding silver nitrate; or
iv) a buffer to maintain the pH at approximately 7 to the compound of Formula (5) in the liquid medium. The process is preferably carried out at a temperature from 0° C. to 150° C. and more preferably from 50° C. to 120° C. and conveniently at the boiling point of the liquid medium.

The process is continued until substantially all the starting materials are consumed. The product is isolated by neutralisation of the reaction mixture, extraction with an organic liquid, separation and evaporation. The product is purified by any convenient means such as distillation or column chromatography.

According to a further feature of the present invention there is provided a process for the preparation of a pyran-2-one of the Formula (10):

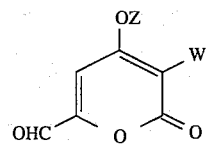

Formula (10)

by oxidation of a pyran-2-one of the Formula (11):

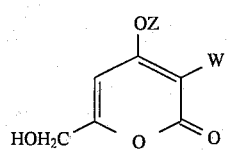

Formula (11)

wherein:

W and Z are as hereinbefore defined.

This process may be performed under the oxidation conditions described above for Formula (7).

According to a further feature of the present invention there is provided a process for the preparation of a pyran-2-one of the Formula (7) by removal of a group W from a pyran-2-one of Formula (6) wherein W and Z are as hereinbefore defined. The removal of the group W may be performed under the conditions described above for removal of the group W from the pyran-2-one of Formula (5).

According to a further feature of the present invention there is provided a process for the preparation of a pyran-2-one of Formula (4) by halogenation of a pyran-2-one of Formula (7). The halogenation may be performed under the conditions described above for halogenating the pyran-2-one of Formula (6).

Halogenation of the pyran-2-one of Formula (6) in which W is —H to give the corresponding pyran-2-one of Formula (5) in which W is —H or halogenation of the pyran-2-one of Formula (5) in which W is —H to give the corresponding pyran-2-one of Formula (8) in which W is —H or halogenation of the pyran-2-one of Formula (8) in which W is —H to give the corresponding pyran-2-one of Formula (9) in which W is —H may be performed under the conditions described above for halogenating the pyran-2-one of Formula (6).

Pyran-2-ones of Formula (5) where X is —I may also be prepared from pyran-2-ones of Formula (5) where X is —Br by halogen exchange in a liquid medium with iodide optionally in the presence of a phase transfer catalyst. The phase transfer catalyst is preferably a tetraalkyl ammonium halide such as tetrabutylammonium bromide. The liquid medium is preferably an organic liquid, more preferably a ketone such as acetone or methylethylketone or a lower alkanol such as ethanol or isopropanol. The iodide is preferably an inorganic iodide such as potassium or sodium iodide. This process forms a further aspect of the present invention.

The pyran-2-one of Formula (5) in which W is —H and Z is —H may be prepared by reaction of an acid chloride of formula XCH₂COCl with keten, followed by cyclisation of the intermediate dioxohexanoic acid chloride to the compound of Formula (5).

The pyran-2-one of Formula (5) in which W is —COCH₂X and Z is —H may be prepared by the self-condensation of 2 equivalents of a beta-keto ester of the formula XCH₂COCH₂COOEt, in which Y is as hereinbefore defined, in a liquid medium such as chloroform in the presence of phosphorus pentoxide, further details are provided in Izv. Akad. Nauk. SSR, Ser. Khim. (1982) 1657.

According to the a further feature of present invention there is provided a process for the preparation of a compound of the Formula (13):

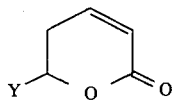

Formula (13)

by the elimination of ZOH from a compound of Formula (1):

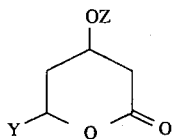

Formula (1)

wherein:

Y and Z are as hereinbefore defined.

A particular utility of the compounds of Formula (13) is that they permit synthesis of trans isomers of compounds of Formula (1) from the cis isomers or from cis/trans mixtures, for example:

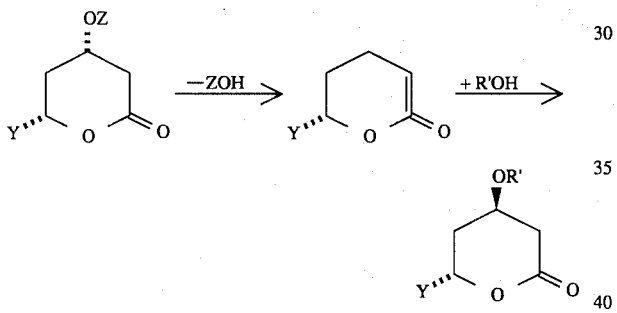

wherein

R' is any of the groups hereinbefore defined for Z or an optionally substituted $C_{1-12}$-alkyl.

For compounds of Formula (1) in which Z is —H the process may be performed by dehydrating the compound of Formula (1) in a liquid medium in the presence of a dehydration catalyst. The liquid medium is preferably an organic liquid, more preferably an aromatic hydrocarbon such as toluene or xylene. Suitable dehydration catalysts are sulphonic acids preferably aromatic sulphonic acids such as p-toluenesulphonic acid. The process is preferably performed at a temperature from 20° C. to 150° C., more preferably from 50° C. to 150° C. and especially at the boiling point of the liquid medium. The reaction is continued until substantially all the starting material is consumed. After washing to remove the catalyst the product is isolated by evaporation of the liquid medium and is purified by any convenient means such as crystallisation, solvent extraction or chromatography.

For compounds of Formula (1) in which Z is for example —SO.OR³, —(CO)OR³, —CO.R³ or —PO.(OR³)₂ the process may be performed by eliminating HOSO₂R³, HO(CO)OR³, HOCO.R³ or HOPO.(OR³)₂ respectively from the compound of Formula (1) by reaction with a base in a liquid medium. Suitable bases are organic nitrogen bases such as triethylamine, 1,8-diazabicyclo[5.4.0]undec-7-ene (DBU) and 1,5-diazabicyclo[4.3.0]non-5-ene (DBN), metal alkoxides, preferably alkali metal alkoxides such as sodium ethoxide or potassium t-butoxide or inorganic bases such as sodium carbonate. The liquid medium is preferably an organic liquid, more preferably a halocarbon such as dichloromethane, an aromatic hydrocarbon such as toluene or an anhydrous dipolar aprotic liquid such as dimethylformamide (DMF) and dimethylsulphoxide (DMSO). The process may optionally be performed in the presence of a phase transfer catalyst. Suitable phase transfer catalysts are alkyl ammonium halides such as tetrabutylammonium bromide and tetramethylammonium bromide or chloride. The process is preferably performed at a temperature from 20° C. to 200° C., more preferably at 30° C. to 100° C. The reaction is continued until substantially all the starting material is consumed. After treatment to remove residual base, the product may be isolated by evaporation of the liquid medium and purified as above.

Elimination of ZOH from an individual enantiomer of Formula (1) by the above process produces a single optical isomer of Formula (13).

In compounds of Formula (1) in which Z is —H the 4-hydroxy group may be converted to a sulphonate ester group by reaction with the corresponding sulphonyl chloride, such as 4-toluenesulphonyl chloride in the presence of pyridine or methanesulphonyl chloride in the presence of triethylamine.

According to a further feature of the present invention there is provided a resolved isomer of the Formula (1) wherein Z and Y are as hereinbefore defined.

A preferred resolved tetrahydropyran-2-one isomer of Formula (1) is of Formula (14):

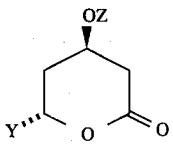

Formula (14)

wherein:

Z is —H or a protecting group; and

Y is formyl or protected formyl.

A further preferred resolved tetrahydropyran-2-one isomer of Formula (1) is of Formula (15):

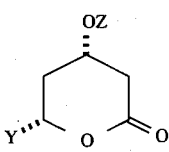

Formula (15)

wherein:

Z is —H or a protecting group; and

Y is formyl or protected formyl.

A further preferred resolved tetrahydropyran-2-one isomer of Formula (1) is of Formula (16):

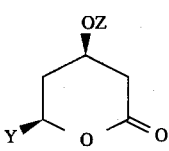

Formula (16)

wherein:

Z is —H or a protecting group; and

Y is formyl or protected formyl.

A further preferred resolved tetrahydropyran-2-one isomer of Formula (1) is of Formula (17):

Formula (17)

[structure: pyran-2-one with OZ at 4-position (dashed bond) and Y at 6-position (wedge)]

Z is —H or a protecting group; and
Y is formyl or protected formyl,
except for (4S,6R) 4-hydroxy-6-di(ethylthio)methyltetrahydropyran-2-one.

According to a further feature of the present invention there is provided a racemate comprising the compounds of Formulae (14) and (17):

Formula (14)

[structure: pyran-2-one with OZ at 4-position and Y at 6-position]

Formula (17)

[structure: pyran-2-one with OZ at 4-position and Y at 6-position]

wherein:

Z is —H or a protecting group; and
Y formyl or protected formyl.

According to a further feature of the present invention there is provided a racemate comprising the compounds of the Formulae (15) and (16):

Formula (15)

[structure: pyran-2-one with OZ at 4-position and Y at 6-position]

Formula (16)

[structure: pyran-2-one with OZ at 4-position and Y at 6-position]

wherein:

Z is —H or a protecting group; and
Y formyl or protected formyl.

According to a further feature of the present invention there is provided a dihydropyran-2-one of the Formula (18):

Formula (18)

[structure: dihydropyran-2-one with OZ and Y]

wherein:

Z is —H or a protecting group; and
Y is formyl or protected formyl.

According to a further feature of the present invention there is provided a resolved dihydropyran-2-one of the Formula (19):

Formula (19)

[structure: dihydropyran-2-one with OZ and Y]

wherein:

Z is —H or a protecting group; and
Y is formyl or protected formyl.

According to a further feature of the present invention there is provided a racemate of dihydropyran-2-ones of Formula (2) wherein Y and Z are as hereinbefore defined.

According to a further feature of the present invention there is provided a pyran-2-one of the Formula (3) wherein Z and Y are as hereinbefore defined.

According to a further feature of the present invention there is provided a pyran-2-one of Formula (4) wherein Z and X are as hereinbefore defined, provided that when Z is —H, X is not —Br or —Cl.

According to a further feature of the present invention there is provided a pyran-2-one of Formula (5) wherein Z, W and X are as hereinbefore defined, provided that when Z is —H and W is —COCH$_3$, X is not —Br.

According to a further feature of the present invention there is provided a pyran-2-one of Formula (6) wherein Z and W are as hereinbefore defined, provided that when Z is —H, W is not —COCH$_3$.

According to a further feature of the present invention there is provided a pyran-2-one of Formula (7) wherein Z is a protecting group.

According to a further feature of the present invention there is provided a pyran-2-one of Formula (8) wherein Z is a protecting group and X and W are as hereinbefore defined provided that when Z is —H and W is —COCH$_3$, X is not —Br.

According to a further feature of the present invention there is provided a pyran-2-one of Formula (10) wherein Z and W are as hereinbefore defined.

According to a further feature of the present invention there is provided a pyran-2-one of Formula (11) wherein Z and W are as hereinbefore defined, provided that when Z is —H, W is not —H or —COCH$_3$.

According to a further feature of the present invention there is provided a pyran-2-one of Formula (13) wherein Y is formyl or protected formyl.

The invention may be illustrated by the following:

EXAMPLE 1 i) 3-Acetyl-6-methyl-4-hydroxypyran-2-one may be deacylated by reaction with 90% sulphuric acid at 130° C. to give 6-methyl-4-hydroxy pyran-2-one;

ii) 6-Methyl-4-hydroxypyran-2-one may be oxidised with selenium dioxide in boiling diglyme to give 6-formyl-4-hydroxypyran-2-one;

iii) The formyl group in 6-formyl-4-hydroxypyran-2-one may be protected by reaction with methanol in the presence of dry hydrogen chloride to give 6-dimethoxymethyl-4-hydroxypyran-2-one;

iv) 6-Dimethoxymethyl-4-hydroxypyran-2-one may be reduced in methanol with hydrogen in the presence of a palladium on carbon catalyst to give 6-dimethoxymethyl-5,6-dihydro-4-hydroxy-pyran-2-one;

v) 6-Dimethyoxymethyl-5,6-dihydro-4-hydroxypyran-2-one may be reduced in methanol with hydrogen in the presence of a Raney nickel catalyst to give 6-dimethoxymethyl-4-hydroxytetrahydropyran-2-one;

vi) 6-Dimethoxymethyl-4-hydroxytetrahydropyran-2-one may be resolved in tetrahydrofuran by transesterification with vinyl acetate in the presence of a lipase at 40° C. according to the scheme:

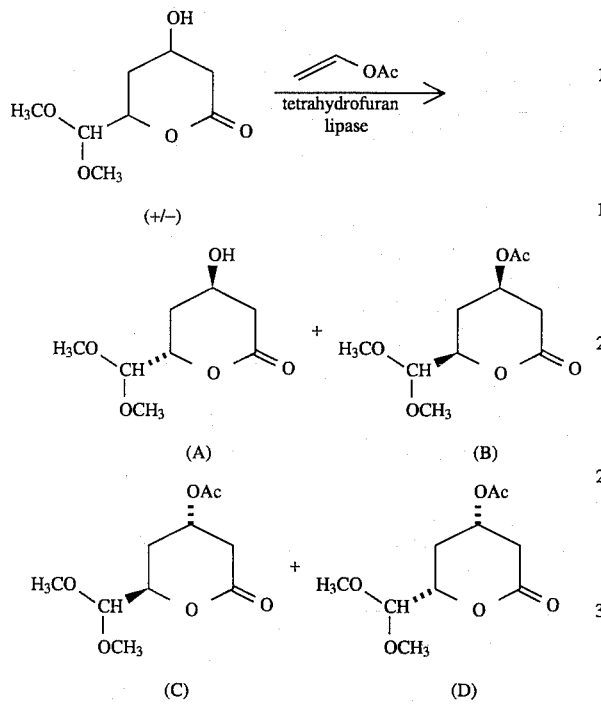

after removing the lipase by filtration and evaporating the volatile solvents by vacuum distillation the crude product may be chromatographed on silica using a mixture of ethylacetate and dichloromethane to obtain the 4-hydroxytetrahydropyran-2-one enantiomer represented by (A).

vii) Repeating vi) above using the trans racemate of 6-dimethoxymethyl-4-hydroxytetrahydropyran-2-one produces the trans isomers (A) and (C).

EXAMPLE 2 i) 6-Methyl-4-hydroxypyran-2-one as produced in Example 1 may be brominated with N-bromosuccinimide, in carbon tetrachloride in the presence of ultraviolet radiation to give 6-dibromomethyl-4-hydroxy-pyran-2-one.

ii) 6-Dibromomethyl-4-hydroxypyran-2-one may be reacted with ethanol in the presence of silver nitrate to give 6-diethoxymethyl-4 -hydroxpyran-2-one.

iii) 6-Diethoxymethyl-4-hydroxypyran-2-one may be further converted according to the method of Example 1 into Compound (E):

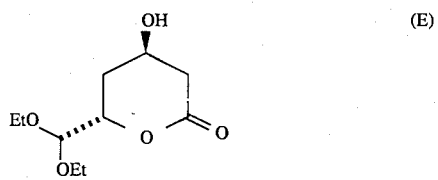

EXAMPLE 3 i) 3-Acetyl-4-hydroxy-6-methylpyran-2-one may be brominated with N-bromosuccinimide in carbon tetrachloride at 40° C. in the presence of ultraviolet radiation to give 3-acetyl-6-dibromomethyl-4-hydroxy pyran-2-one.

ii) 3-Acetyl-4-hydroxy-6-bromomethylpyran-2-one may be reacted with ethanol in the presence of silver nitrate to give 3-acetyl-6 -diethoxymethyl-4-hydroxypyran-2-one.

iii) 3-Acetyl-6-diethoxymethyl-4-hydroxypyran-2-one may be reacted with aqueous acid to give 3-acetyl-6-formyl-4-hydroxypyran-2-one.

We claim:

1. A resolved isomer of the Formula (1):

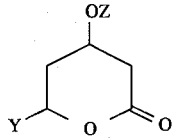

Formula (1)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

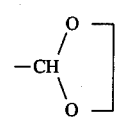

in which each R independently is —H, optionally substituted C$_{1-12}$ -alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ and —NR$_2$.

2. A resolved tetrahydropyran-2-one isomer is of Formula (14):

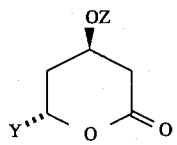

Formula (14)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

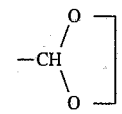

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ and —NR$_2$.

3. A resolved tetrahydropyran-2-one isomer is of Formula (15):

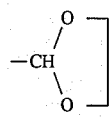

Formula (15)

wherein:

Z is H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NH-COMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NH-COMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

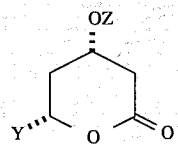

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$, or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, 'N(SiMe$_3$)$_2$ and —NR$_2$.

4. A resolved tetrahydropyran-2-one isomer is of Formula (16):

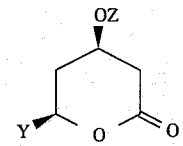

Formula (16)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NH-COMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NH-COMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

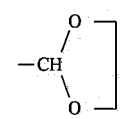

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$alkyl, C$_{1-6}$-alkoxy, cyclohexyl, phenyl, —NO$_2$, —OH, —CN, —Cl, —Br, —F, —NHCOMe, —N(SiMe$_2$)$_2$ and —NR$_2$.

5. A resolved tetrahydropyran-2-one isomer is of Formula (17):

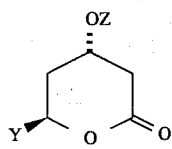

Formula (17)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —C$_1$, —Br, —F, —OH, —CN, cyclohexyl, phenyl, —NHCOMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

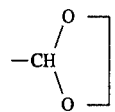

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ and —NR$_2$ except for (4S, 6R) 4-hydroxy-6-di(ethylthio)methyltetrahydropyran-2-one.

6. A racemate comprising the compounds of Formulae (14) and (17):

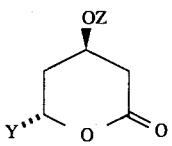

Formula (14)

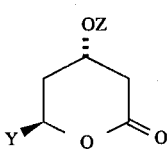

Formula (17)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

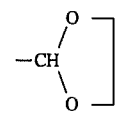

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ and —NR$_2$.

7. A racemate comprising the compounds of the Formulae (15) and (16):

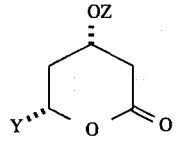

Formula (15)

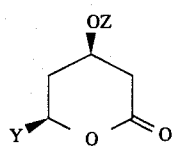

Formula (16)

wherein:

Z is —H or a protecting group selected from the group consisting of —PO.(OR$^3$)$_2$, —CO.R$^3$, —SO.OR$^3$, —NO$_2$ and —CO.OR$^3$ in which each R$^3$ independently is optionally substituted C$_{1-12}$-alkyl, optionally substituted C$_{2-12}$-alkenyl or optionally substituted phenyl in which each of the alkyl and alkenyl groups represented by R$^3$ is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is —H, C$_{1-12}$-alkyl, C$_{2-12}$-alkenyl or phenyl and in which each of the phenyl groups represented by R$^3$ is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ or —NR$_2$; and Y is formyl or protected formyl selected from the group consisting of —CH(OR)$_2$, —CH(SR)$_2$, —CH(OR)(SR), oxazolidine, imidazolidine, thiazolidine, bisulphite, cyanohydrin, hydrazone, oxime, O-acylcyanohydrin, O-tetrahydropyran-2-ylcyanohydrin, O—SiR$^3$ cyanohydrin and

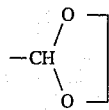

in which each R independently is —H, optionally substituted C$_{1-12}$-alkyl, optionally substituted C$_{2-12}$-alkenyl or optionally substituted phenyl in which each of the alkyl and alkyl groups is optionally substituted by C$_{1-6}$-alkoxy, —Cl, —Br, —F, —OH, —CN, cyclohexyl, phenyl, —NHCOMe, —N(SiMe$_3$)$_2$ or —NR$_2$ in which R is selected from —H, C$_{1-12}$-alkyl, C$_{2-12}$-alkenyl and phenyl and in which each of the phenyl groups represented by R is optionally substituted by C$_{1-6}$-alkyl, C$_{1-6}$-alkoxy, cyclohexyl, phenyl, —NO$_2$, —OH, —CN, —Cl, —Br, —F, —NHCOMe, —N(SiMe$_3$)$_2$ and —NR$_2$.

* * * * *